(12) United States Patent
Volkmer et al.

(10) Patent No.: US 10,143,484 B2
(45) Date of Patent: Dec. 4, 2018

(54) MEDICAL INSTRUMENT

(71) Applicant: Karl Storz SE & Co. KG, Tuttlingen (DE)

(72) Inventors: Dominik Volkmer, Fridingen (DE); Jochen Stefan, Wald (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 248 days.

(21) Appl. No.: 14/940,848

(22) Filed: Nov. 13, 2015

(65) Prior Publication Data
US 2016/0135830 A1     May 19, 2016

(30) Foreign Application Priority Data
Nov. 14, 2014 (DE) .................. 10 2014 016 790

(51) Int. Cl.
*A61B 17/29* (2006.01)
*A61B 17/00* (2006.01)
*A61B 34/30* (2016.01)

(52) U.S. Cl.
CPC .......... *A61B 17/2909* (2013.01); *A61B 17/29* (2013.01); *A61B 2017/00398* (2013.01); *A61B 2017/293* (2013.01); *A61B 2017/2927* (2013.01); *A61B 2017/2929* (2013.01); *A61B 2034/305* (2016.02)

(58) Field of Classification Search
CPC .......... A61B 17/29; A61B 2017/00398; A61B 2017/2927; A61B 2017/2929; A61B 2017/293; A61B 2034/305; A61B 17/2909
See application file for complete search history.

(56) References Cited

U.S. PATENT DOCUMENTS

| | | | |
|---|---|---|---|
| 4,645,373 A | 2/1987 | Purdy | |
| 5,607,449 A | 3/1997 | Tontarra | |
| 2010/0331857 A1 | 12/2010 | Doyle et al. | |
| 2012/0310222 A1 | 12/2012 | Naito | |
| 2014/0277107 A1 | 9/2014 | Ishida et al. | |

FOREIGN PATENT DOCUMENTS

| | | |
|---|---|---|
| WO | 2011156168 A1 | 12/2011 |
| WO | 2013154158 A1 | 10/2013 |
| WO | 2013154700 A1 | 10/2013 |

OTHER PUBLICATIONS

German Search Report Application No. 10 2014 016 790.9 Completed: Sep. 9, 2015; dated Sep. 9, 2015 8 pages.
European Search Report Application No. EP 15003125.0 Completed: Dec. 1, 2015;dated: Dec. 7, 2015 5 pages.

*Primary Examiner* — Jonathan Miles
*Assistant Examiner* — George J Ulsh
(74) *Attorney, Agent, or Firm* — Whitmyer IP Group LLC (57) ABSTRACT

A medical instrument with a hollow shaft and at the distal end a tool actuated via a spring-loaded pull cable, wherein the tool is rotatable about the longitudinal axis of the shaft and is mounted such that it can be angled with respect to the longitudinal axis of the shaft. Actuation of the pull cable and rotation and angled positioning of the tool take place via separate drives, which are arranged on a handle. An anti-twist means protects the pull cable against torsion.

10 Claims, 7 Drawing Sheets

MEDICAL INSTRUMENT

FIELD OF THE INVENTION

The invention relates to a medical instrument with a hollow shaft, at the proximal end of which a handle is arranged, and at the distal end of which a tool tip is arranged, wherein the tool tip has a tool that can be actuated via a spring-loaded pull cable, and wherein the tool tip is rotatable about the longitudinal axis of the shaft and is mounted on the shaft such that it can be angled with respect to the longitudinal axis of the shaft, wherein the actuation of the pull cable and the rotation and angled positioning of the tool tip each take place via separate drives, which are arranged on the handle.

BACKGROUND OF THE INVENTION

To allow the operator a high degree of freedom of movement when using a medical holding and/or gripping instrument, it is known from practice that, in addition to the simple actuation of a distal tool by opening and closing of the jaw parts, the tool tip of the medical instrument can be configured such that said tool tip is rotatable about the longitudinal axis of the instrument and is pivotable with respect to the longitudinal axis of the instrument.

A medical instrument of the type in question is known from WO 2013/154158 A1, for example. In this known medical instrument, frictional forces occur and create a danger of the pull cable being subjected to torsion during the rotation of the tool tip, as a result of which the service life of the pull cable may be impaired, in particular with an alternating direction of rotation of the tool tip.

SUMMARY OF THE INVENTION

Proceeding from this, it is the object of the invention to configure a medical instrument of the aforementioned type in such a way as to ensure that the pull cable is mounted in a manner free of torsion.

According to the invention, the solution to this problem is characterized in that an anti-twist means protecting the pull cable against torsion is arranged on the distal end of the pull cable arranged in the tool tip rotatable about the longitudinal axis of the shaft, wherein the anti-twist means is mounted at least partially on the non-rotating shaft.

By the use of the anti-twist means according to the invention, which is mounted at least partially on the non-rotating shaft, i.e. on the stationary part of the instrument, it is reliably possible for the first time to prevent the pull cable from being subjected to a torsional load.

According to a practical embodiment of the invention, it is proposed that the anti-twist means is constructed in two parts and is composed of a first part connected to the pull cable and of a second part mounted on the non-rotatable shaft, wherein both parts of the anti-twist means are operatively connected to each other in such a way that the second part blocks a rotation of the first part relative to the second part.

To form the two parts of the anti-twist means, the invention proposes that the first part of the anti-twist means connected to the pull cable is designed as a tube coaxially enclosing the pull cable, and that the second part of the anti-twist means mounted on the shaft is designed as a sleeve engaging at least partially around the tube.

To ensure that the pull cable is movable in the axial direction, as is necessary for actuating the distal tool, the invention further proposes that the two parts of the anti-twist means are movable relative to each other in the direction of the longitudinal axis of the shaft.

According to a first embodiment for forming the two-part anti-twist means, it is proposed, according to the invention, that the tube forming the first part of the anti-twist means has an outer contour that is non-circular in cross section, and that the sleeve forming the second part of the anti-twist means has, in the area engaging around the tube, an inner surface contour which forms a corresponding matching contour to the outer contour of the tube in this engaged area.

By virtue of these two structural parts, namely tube and sleeve, bearing on each other with form-fit contact at least in some areas, a possible rotation of the tube about the longitudinal axis of the shaft inside the sleeve is prevented.

The non-circular outer contour of the tube, preventing rotation of the tube relative to the sleeve, and the corresponding matching contour of the sleeve are obtained, according to the invention, by virtue of the fact that the tube forming the first part of the anti-twist means has, on its outer circumferential surface, two flat portions extending in the direction of the longitudinal axis of the shaft, and that the sleeve forming the second part of the anti-twist means has, in the area engaging around the tube, two corresponding flat portions on the inner face directed toward the tube, wherein the flat portions formed on the outer circumferential surface of the tube are advantageously offset to each other by 180°.

By virtue of the plane flat portions of the tube and the plane flat portions of the sleeve bearing on each other, a rotation of the pull cable secured in the tube is reliably and permanently suppressed during the rotation of the tool tip about the longitudinal axis of the shaft.

Finally, in a second embodiment for forming the two-part anti-twist means, it is proposed that an oblong hole extending in the direction of the longitudinal axis of the shaft is formed in the tube forming the first part of the anti-twist means, and that a radially extending pin protruding into the oblong hole of the tube is arranged in the sleeve forming the second part of the anti-twist means.

BRIEF DESCRIPTION OF THE DRAWINGS

Further features and advantages of the invention are set forth in the appended drawings, in which two illustrative embodiments of a medical instrument according to the invention are shown purely by way of example, without limiting the invention to these illustrative embodiments. In the drawings.

DETAILED DESCRIPTION OF THE INVENTION

Figure 1:
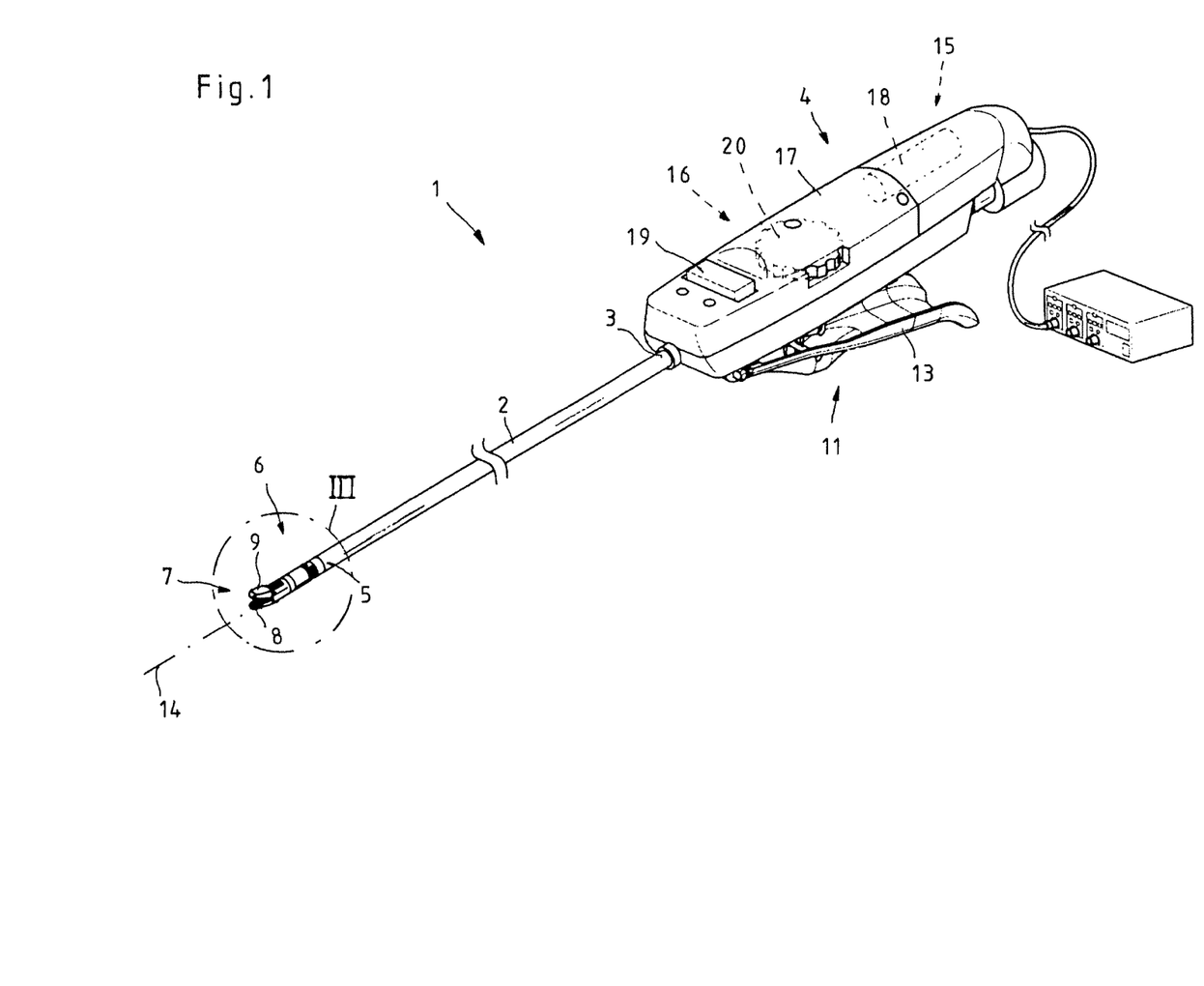
FIG. 1 shows a perspective side view of a medical instrument according to the invention.

FIG. 1 shows a perspective side view of a medical instrument 1 which is composed principally of a hollow shaft 2, a handle 4 arranged at the proximal end 3 of the shaft 2, and a tool tip 6 arranged at the distal end 5 of the shaft 2.

For its part, the tool tip 6 has, at its distal end, a tool 7 which, in the embodiment shown, is composed of a stationary jaw part 8 and of a jaw part 9 that is pivotable relative to the stationary jaw part 8.

As an alternative to the depicted design of the tool 7 as a gripping and holding tool composed of two jaw parts 8 and 9, the tool can also be designed as a cutting tool, for example. It is likewise possible for both jaw parts of the tool 7 to be designed as pivotable jaw parts 9.

Figure 2:
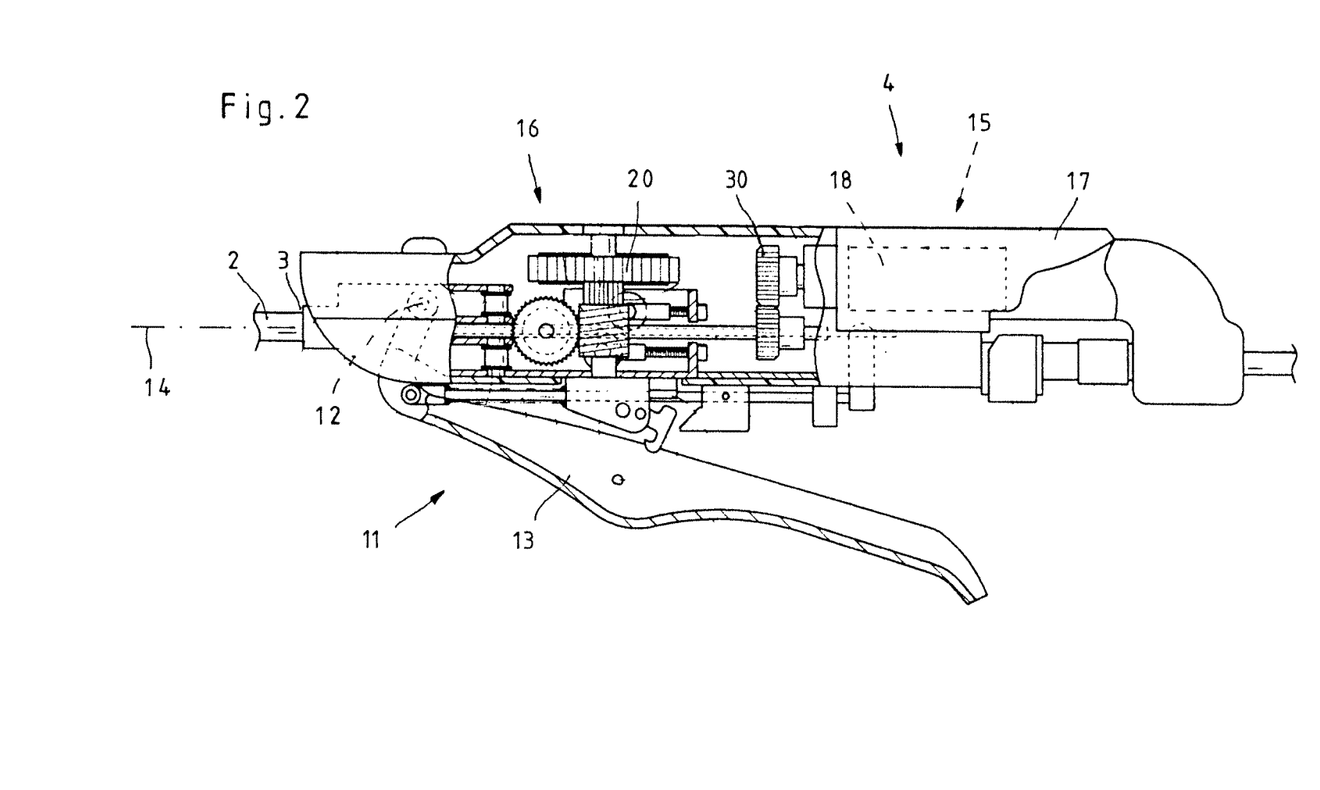
FIG. 2 shows a partially sectioned side view of the handle of the medical instrument according to FIG. 1.

The jaw parts 8 and 9 of the tool 7 are adjustable between an open starting position and a closed holding position. The actuation of the tool 7, i.e. in the embodiment shown the pivoting of the jaw part 9, takes place via a pull cable 10, which is mounted in the hollow shaft 2 and is operatively connected to a drive 11 arranged on the handle 4. The drive 11 for actuating the tool 7 is designed as a grip 13, which is mounted on the handle 4 so as to be pivotable about a pivot axis 12.

In addition to the actuation of the tool 7 via the drive 11, the tool tip 6 is mounted on the distal end 5 of the shaft 2 in such a way as to be rotatable about the longitudinal axis 14 of the shaft 2 and to be angled with respect to the longitudinal axis 14 of the shaft 2. The rotating and angled positioning of the tool tip 6 each take place via separate drives 15 and 16 arranged on the handle 4.

As an alternative to the depicted pivoting of the tool tip 6 relative to the longitudinal axis 14 of the shaft 2 to the right and to the left, it is likewise possible to configure the medical instrument 1 such that the tool tip 6 is pivotable upward and downward relative to the longitudinal axis 14 of the shaft 2.

The drive 15 for rotating the tool tip 6 about the longitudinal axis 14 of the shaft 2 is designed as an electric or pneumatic motor 18, which is arranged in the handle housing 17 and which can be activated, via a toggle switch 19 arranged at the distal end of the handle 4, in order to cause the tool tip 6 to rotate about the longitudinal axis 14 of the shaft 2 either clockwise or counterclockwise.

The drive 16 for pivoting the tool tip 6 relative to the longitudinal axis 14 of the shaft 2 is configured as a rotary wheel 20 which protrudes laterally on both sides through the handle 4 and which, when rotated, causes the tool tip 6 to be pivoted relative to the longitudinal axis 14 of the shaft 2, according to the direction of rotation of the rotary wheel 20.

Figure 3:
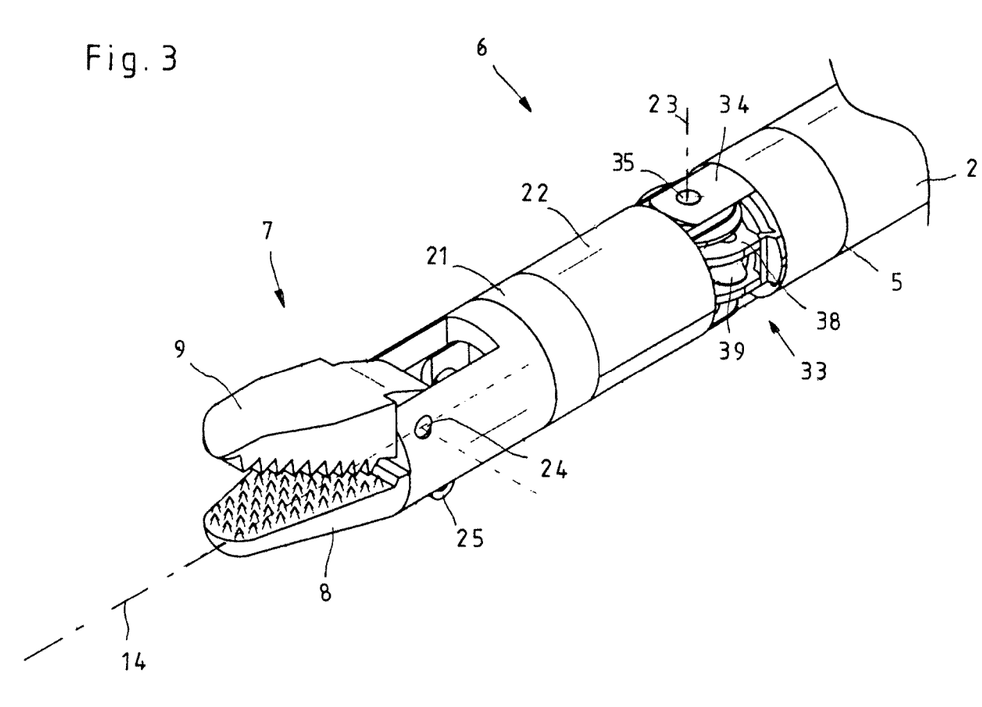
FIG. 3 shows a perspective side view of detail III according to FIG. 1, depicting a first embodiment of the anti-twist means.
Figure 4:
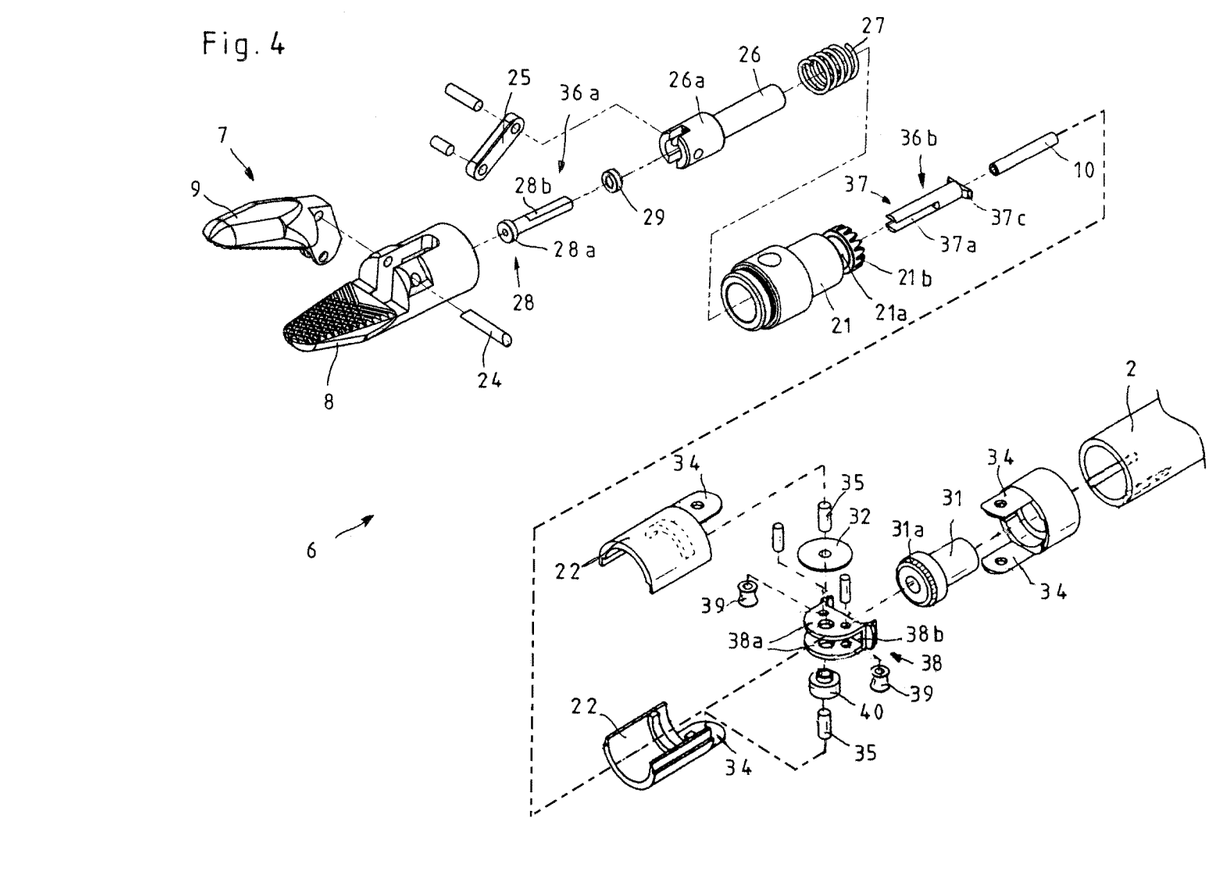
FIG. 4 shows an exploded drawing of the view according to FIG. 3.
Figure 5:
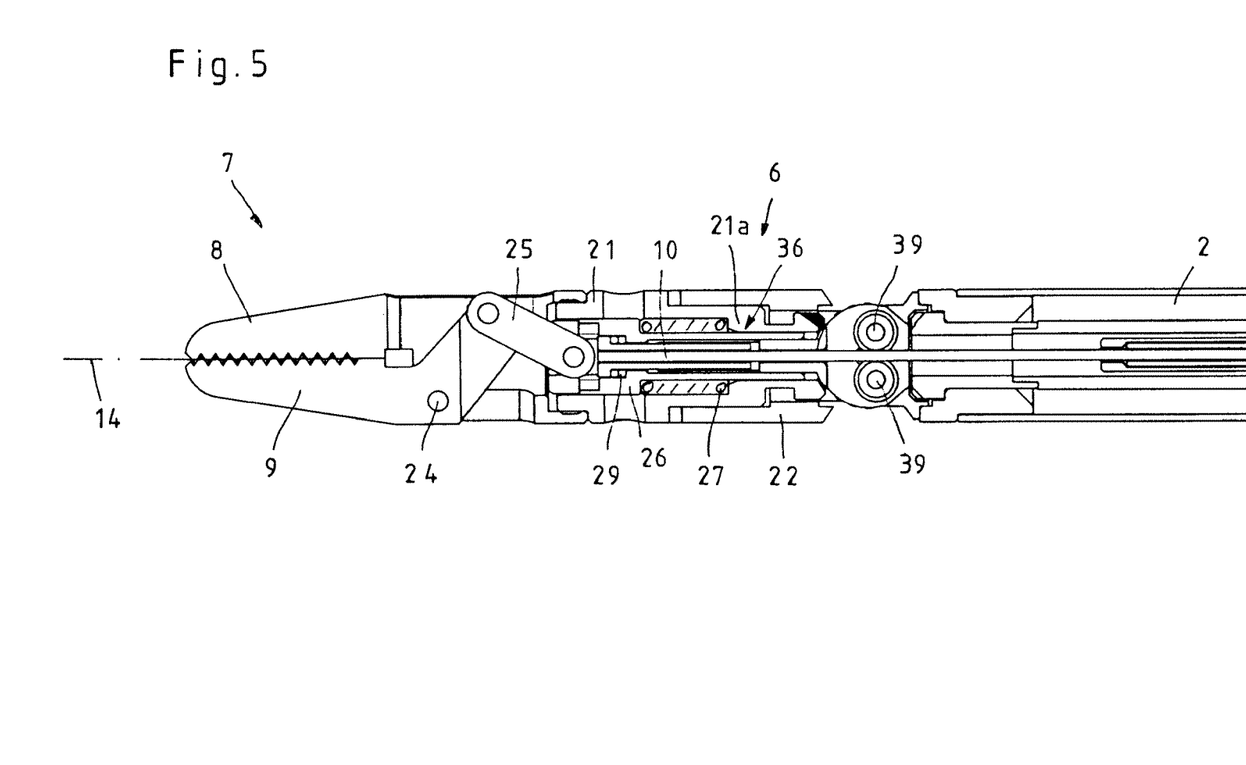
FIG. 5 shows a longitudinal section through the view according to FIG. 3.

FIG. 3 to FIG. 5 show a perspective view of the distal end 5 of the shaft 2 and of the tool tip 6 provided with the tool 7, an exploded view of this instrument portion, and a longitudinal section through this instrument portion.

As will be clear from the views in FIGS. 3 to 5, the tool tip 6 comprises the tool 7, with the jaw parts 8 and 9 to be opened and closed, a sleeve 21 which is rotatable about the longitudinal axis 14 of the shaft 2 and which is fixedly connected to the stationary jaw part 8 of the tool 7, and a rotation unit 22 via which the tool tip 6 is pivotable about the pivot axis 23 relative to the longitudinal axis 14 of the shaft 2.

As will be clear from FIG. 5, the stationary jaw part 8 and the pivotable jaw part 9 are connected to each other via a pin 24, which at the same time forms the pivot axis about which the pivotable jaw part 9 is pivotable relative to the stationary jaw part 8 in order to open and close the tool 7. In the illustrative embodiment shown, the actuation of the pivotable jaw part 9 by the pull cable 10 takes place indirectly via an articulated lever 25, which is mounted with one end pivotably on the pivotable jaw part 9 and which, with its other end, is mounted pivotably on a transmission element 26, which serves to receive and support the distal end of the pull cable 10.

As will be clear from FIG. 5, the transmission element 26 is designed as a hollow tube, which is mounted in the sleeve 21 of the tool tip 6 and which has, at the distal end, a head 26a radially widening the external diameter of the tube. The hollow tube forming the transmission element 26 is mounted in the sleeve 21 so as to be axially movable in the direction of the longitudinal axis 14 of the shaft 2. Mounted between the sleeve 21 and the transmission element 26 is a spring element 27 in the form of a compression spring, which is supported at the distal end on the head 26a of the transmission element 26 and bears at the proximal end on a shoulder 21a that reduces the internal diameter of the sleeve 21, as a result of which the transmission element 26 is pretensioned in the distal direction by the spring element 27.

Arranged in the interior of the hollow transmission element 26 is a further hollow tube 28 in which the distal end of the pull cable 10 is fixed, for example by soldering. At its distal end, the tube 28 serving to receive the pull cable 10 has a head 28a which radially widens the external diameter of the tube 28 and via which the tube 28 on the inner face of the transmission element 26 bears on the head 26a of the transmission element 26, wherein a rotary bearing 29, preferably made of polyether ether ketone (PEEK), is advantageously arranged between the head 28a of the tube 28, connected to the pull cable 10, and the head 26a of the transmission element 26.

With this construction as described above, the actuation of the pivotable jaw part 9 of the tool 7 can be described as follows:

At its distal end, the pull cable 10 serving to actuate the pivotable jaw part 9 is operatively connected to the pivotable jaw part 9 of the tool 7 via the tube 28, the transmission element 26 and the articulated lever 25. At its proximal end, the pull cable 10 is operatively connected to the pivotable grip 13 of the handle 4.

In the unloaded starting position, the spring element 27 arranged coaxially on the tube 28 presses the transmission element 26 in the distal direction, as a result of which the pivotable jaw part 9 of the tool 7 is transferred to the open starting position via the articulated lever 25. The spring bias of the transmission element 26 in the distal direction also at the same time has the effect that the tube 28 connected fixedly to the pull cable 10, and therefore also the pull cable 10, is pretensioned in the distal direction. In this position of the pull cable 10, the grip 13 pivotable about the pivot axis 12 is also located in the starting position, in which said grip 13 is spaced apart in the radial direction from the handle 4.

When the person operating the medical instrument 1 takes hold of the grip 13 and presses it toward the handle 4, this shifting of the grip 13 exerts a proximally directed tensile force on the pull cable 10, via a transmission mechanism not described in detail.

This tensile loading of the pull cable 10 in the proximal direction has the effect that, by way of the head 28a of the tube 28 in which the pull cable 10 is fixed, the transmission element 26 is pulled proximally counter to the force of the spring element 27, as a result of which the articulated lever 25 connected to the transmission element 26 is also moved in the proximal direction. This shifting of the articulated lever 25 in the proximal direction effects the transfer of the pivotable jaw part 9 of the tool 7 to the closed working position.

As soon as the person operating the medical instrument 1 releases the grip 13 of the handle 4 again, the spring element 27 presses both the pivotable jaw part 9 and also the grip 13 back into the aforementioned starting position, in which the tool 7 is opened.

In addition to the opening and closing of the jaw parts 8 and 9 of the tool 7 on the distal end of the tool tip 6, the tool tip 6 is rotatable about the longitudinal axis 14 of the shaft 2 and is mounted on the distal end 5 of the shaft 2 in such a way as to be able to be angled with respect to the longitudinal axis 14 of the shaft 2.

The structure of these rotating and pivoting mechanisms can be seen in particular in FIG. 3 to FIG. 5.

The rotation of the tool tip 6 about the longitudinal axis 14 of the shaft 2 is driven via the electrically or pneumatically operated motor 18 arranged in the handle 4, which motor 18 can be activated via flange-mountable outer attachments and can be switched on and off via the toggle switch 19.

The rotation movement generated by the motor 18 is transmitted to a toothed gear 30 arranged in the handle housing 17, which toothed gear 30 drives a sleeve 31 arranged in the shaft 2 such that said sleeve 31 rotates about the longitudinal axis 14 of the shaft 2. At the distal end of the sleeve 31, i.e. the end located at the distal end 5 of the shaft 2, a bevel gear toothing 31a is formed on the sleeve 31.

As will be clear from FIG. 4, the bevel gear toothing 31a of the sleeve 31 meshes with a bevel gear wheel 32 that forms the connection between the distal end 5 of the shaft 2 and the tool tip 6.

As will be clear from FIGS. 3 and 5, a gap 33 is formed between the distal end 5 of the shaft 2 and the tool tip 6, and, in the embodiment of the medical instrument 1 shown, said gap 33 is bridged by two respective brackets 34 which, oriented from the radial outer edge of the distal end 5 of the shaft 2 in the direction of the longitudinal axis 14 of the shaft 2, protrude distally in the direction of the tool tip 6 and, oriented from the radial outer edge of the proximal end of the rotation unit 22 in the direction of the longitudinal axis 14 of the shaft 2, protrude proximally in the direction of the shaft 2. These two respective brackets of the shaft 2 and of the rotation unit 22 are offset to each other by 180° and, in the overlap area, are connected to each other by bolts 35.

One of these bolts 35 at the same time forms the bearing bushing for the bevel gear wheel 32. On sides of the tool tip 6, the bevel gear wheel 32 meshes with a bevel gear toothing 21b, which is formed on the proximal end of the sleeve 21.

With this construction as described above, the operation of the rotation of the tool tip 6 about the longitudinal axis 14 of the shaft 2 can be described as follows:

As soon as the person operating the medical instrument 1 has actuated the toggle switch 19, the motor 18 is switched on and begins to generate a rotation movement. This rotation movement is transmitted by the toothed gear 30 to the sleeve 31 arranged in the interior of the shaft 2, such that the sleeve 31 rotates about the longitudinal axis 14 of the shaft 2. The rotation of the sleeve 31 is transmitted via the distal bevel gear toothing 31a of the sleeve 31 to the bevel gear wheel 32 and from there via the proximal bevel gear toothing 21b of the sleeve 21 to the sleeve 21 arranged on the tool tip 6, such that the sleeve 21 rotates about the longitudinal axis 14 of the shaft 2.

On account of the fixed connection of the sleeve 21 to the stationary jaw part 8 of the tool 7, the whole tool 7 also rotates about the longitudinal axis 14 of the shaft 2.

Depending on the direction in which the toggle switch 19 is actuated, the rotation of the tool tip 6 about the longitudinal axis 14 of the shaft 2 takes place either clockwise or counterclockwise. In the depicted embodiment of the medical instrument 1, there is no limit on the degree of the rotation angle.

Moreover, during the rotation of the tool tip 6 about the longitudinal axis 14 of the shaft 2, it is possible for the jaw parts 8 and 9 of the tool 7 to be closed and opened again by actuation of the grip 13 mounted on the handle 4.

Despite the use of the rotary bearing 29 for mounting the distal end of the pull cable 10 in the transmission element 26, there is a danger, during the rotation of the tool tip 6 about the longitudinal axis 14 of the shaft 2, of the pull cable 10 being subjected to torsion on account of the frictional forces that arise. These torsional forces, which in particular occur in alternating directions of rotation, could greatly curtail the useful life of the pull cable 10.

In order to ensure that the pull cable 10 is mounted in the rotatable tool tip 6 in such a way as to be permanently free of torsion, the depicted medical instrument 1 is provided with an anti-twist means 36 that suppresses any conjoint rotation of the pull cable 10 along with the tool tip 6 rotating about the longitudinal axis 14 of the shaft 2.

Figure 6:
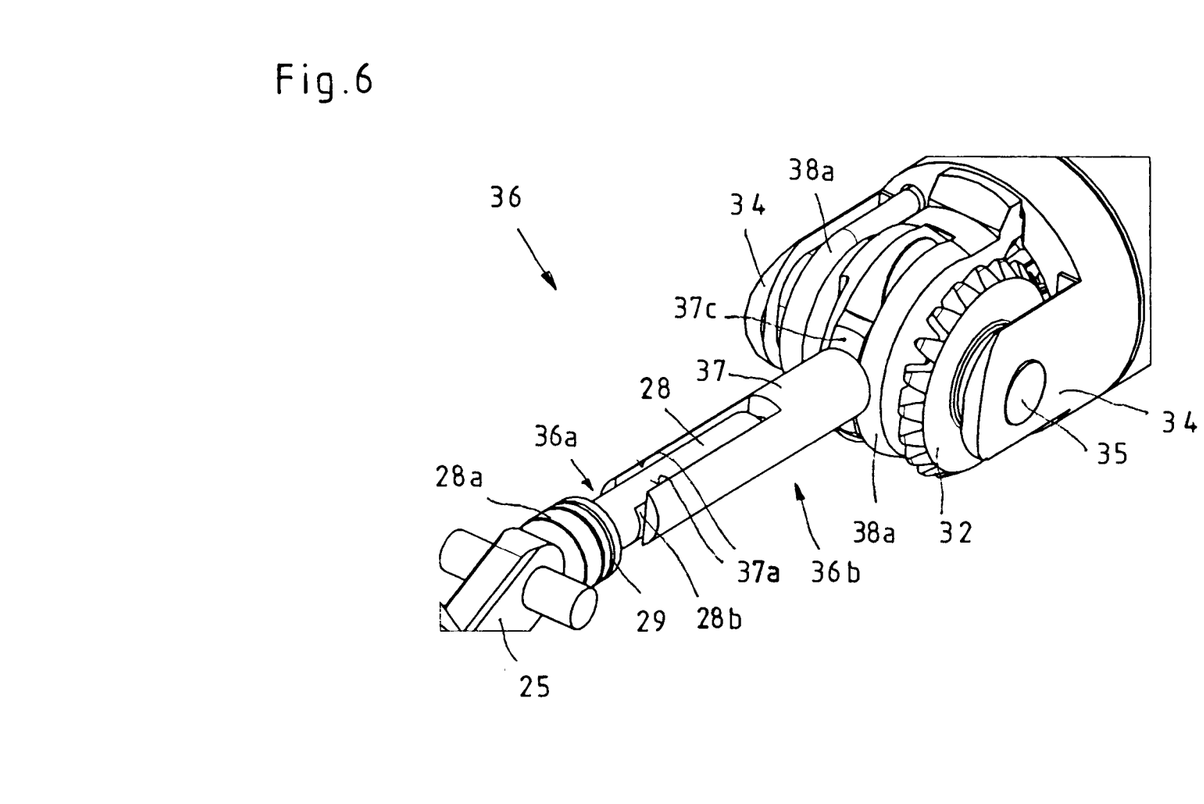
FIG. 6 shows a cut-open and enlarged detail view of the anti-twist means according to FIG. 3.
Figure 7:
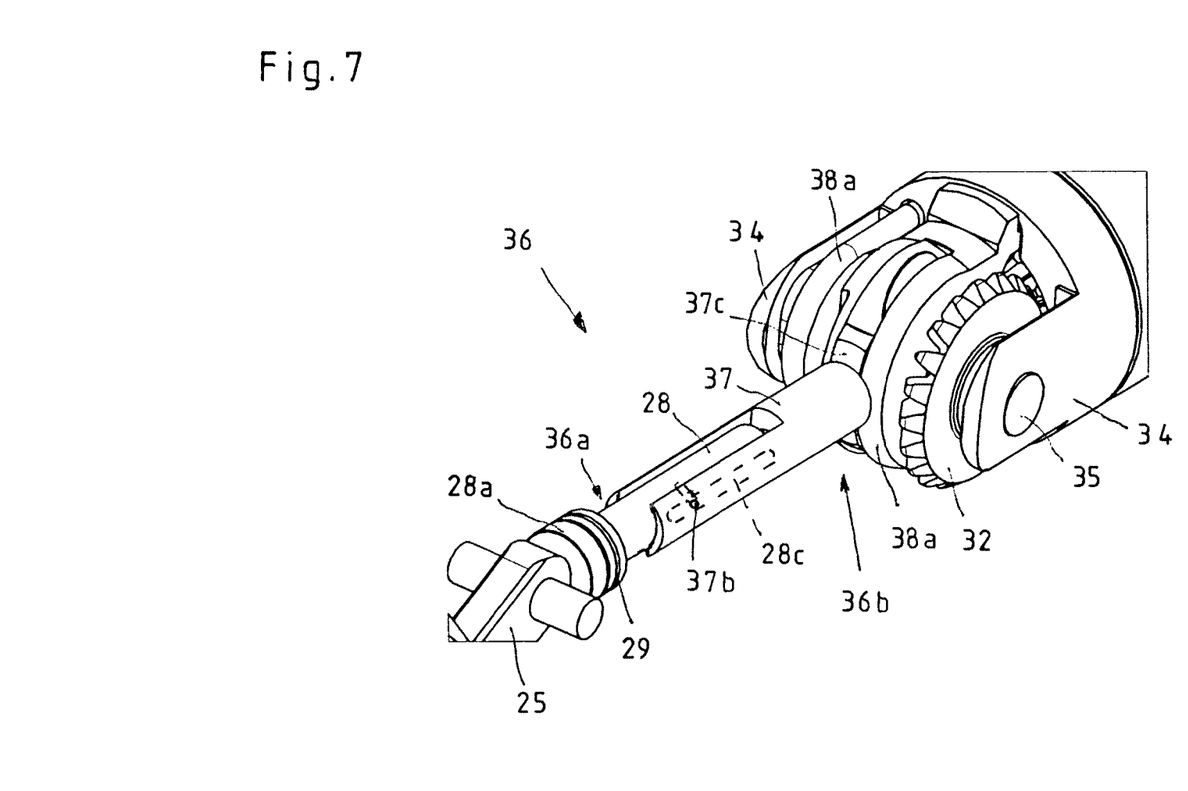
FIG. 7 shows a view according to FIG. 6, but depicting a second embodiment of the anti-twist means.

As will be clear from FIGS. 4, 6 and 7, the anti-twist means 36 in the depicted embodiment is constructed in two parts, being composed of a first part 36a connected to the pull cable 10 and of a second part 36b mounted on the non-rotatable shaft 2.

While the first part 36a of the anti-twist means 36 connected to the pull cable 10 is formed by the tube 28 which coaxially encloses the distal end of the pull cable 10 and in which the pull cable 10 is fixed, the second part 36b of the anti-twist means 36 mounted on the shaft 2 is designed as a sleeve 37 that engages at least partially around the tube 28.

For protecting the pull cable 10 against torsion, it is imperative that both parts 36a and 36b of the anti-twist means 36 are operatively connected to each other in such a way that the second part 36b mounted on the non-rotatable shaft 2 blocks a rotation of the first part 36a, connected to the pull cable 10, relative to the second part 36b.

As will be seen in particular from FIG. 6, this blocking of a possible rotation of the first part 36a of the anti-twist means 36 relative to the second part 36b of the anti-twist means 36, in the first embodiment of the anti-twist means 36 shown in this figure, is obtained by virtue of the fact that the tube 28 forming the first part 36a of the anti-twist means 36 has an outer contour of non-circular cross section, and that the sleeve 37 forming the second part 36b of the anti-twist means 36 has, in the area engaging around the tube 28, an inner surface contour, which forms a corresponding matching contour to the outer contour of the tube 28 in this engaged area. By virtue of these two structural parts, namely tube 28 and sleeve 37, bearing on each other with form-fit contact at least in some areas, a possible rotation of the tube 28 about the longitudinal axis 14 of the shaft 2 inside the sleeve 37 is prevented.

In the depicted first embodiment of the anti-twist means 36, the non-circular outer contour of the tube 28, preventing rotation of the tube 28 relative to the sleeve 37, and the corresponding matching contour of the sleeve 37 are obtained by virtue of the fact that the tube 28 forming the first part 36a of the anti-twist means 36 has, on its outer circumferential surface, two flat portions 28b extending in the direction of the longitudinal axis 14 of the shaft 2, and that the sleeve 37 forming the second part 36b of the anti-twist means 36 has, in the area engaging around the tube 28, two corresponding flat portions 37a on the inner face directed toward the tube 28. The flat portions 28b formed on the outer circumferential surface of the tube 28 are advantageously offset to each other by 180°.

By virtue of the plane flat portions 28b of the tube 28 and the plane flat portions 37a of the sleeve 37 bearing on each other, a rotation of the pull cable 10 secured in the tube 28 is reliably and permanently suppressed during the rotation of the tool tip 6 about the longitudinal axis 14 of the shaft 2.

According to the second embodiment for forming the anti-twist means 36, as shown in FIG. 7, an oblong hole 28c extending in the direction of the longitudinal axis 14 of the shaft 2 is formed in the tube 28 forming the first part 36a of the anti-twist means 36, into which oblong hole 28c there protrudes a radially directed pin 37b arranged in the sleeve 37 which forms the second part 36b of the anti-twist means 36.

The blocking of a possible rotation of the first part 36a of the anti-twist means 36 relative to the second part 36b of the anti-twist means 36, in the second embodiment of the anti-twist means 36 shown in this figure, is obtained by virtue of the fact that the pin 37b, which is arranged in the interior of the sleeve 37 connected to the non-rotatable shaft 2, enters the oblong hole 28c, formed in the tube 28 connected to the cable pull 10, and thereby prevents the tube 28 from being possibly rotated about the longitudinal axis 14 of the shaft 2 on account of the rotation of the tool tip 6.

Since the pull cable 10 has to be able to execute an axial movement in the direction of the longitudinal axis 14 of the shaft 2 in order to open and close the tool 7, it is additionally indispensable, for the formation of the anti-twist means 36, that the pull cable 10 has to be arranged to be axially movable inside the anti-twist means 36.

As will be seen from the two embodiments for formation of the anti-twist means 36 as shown in FIGS. 6 and 7, both parts 36a and 36b of the anti-twist means 36 are movable relative to each other in the direction of the longitudinal axis 14 of the shaft 2. In the embodiment shown in FIG. 6, the flat portions 28b of the tube 28, which extend in the direction of the longitudinal axis 14 of the shaft, and the similarly extending flat portions 37a of the sleeve 37 permit this axial movement of tube 28 and sleeve 37 relative to each other.

In the embodiment shown in FIG. 7, this axial movement of tube 28 and sleeve 37 relative to each other is permitted by the oblong hole 28c of the tube 28, extending in the direction of the longitudinal axis 14 of the shaft, and by the pin 37b of the sleeve 37 arranged therein.

In order to mount the sleeve 37 securely against turning on the distal end 5 of the non-rotating shaft 2, the sleeve 37 has, at its proximal end, a base 37c with which the sleeve is mounted in a bearing block 38. As will be seen from FIGS. 3 and 4, the bearing block is arranged in the gap 33 between the distal end 5 of the shaft 2 and the proximal end of the tool tip 6, between the brackets 34 bridging the gap 33, wherein the bolts 35 connecting the brackets 34 to each other are mounted at their ends in the bearing block 38. The pivot axis 23, about which the tool tip 6 is pivotable relative to the longitudinal axis 14 of the shaft 2, is formed by the bolts 35.

The bearing block 38 is designed to be U-shaped in the side view, such that the two parallel sides 38a extend in the distal direction, and the web 38b connecting the two sides 38a to each other bears flat on the distal end 5 of the shaft 2. The sides 38a of the bearing block 38 are semicircular in plan view.

In the space between the two parallel sides 38a of the bearing block 38, two guide rollers 39 are arranged to the right and left of the longitudinal axis 14 of the shaft 2. The pull cable 10 extends from the shaft 2, through the web 38b of the bearing block 38, to the tool tip 6.

With this construction as described above, the operation of the pivoting of the tool tip 6 relative to the longitudinal axis 14 of the shaft 2 can be described as follows:

When the person operating the medical instrument 1 actuates the rotary wheel 20 mounted on the handle 4, a transmission element directly operatively connected to the rotary wheel 20, and in the form of a Bowden wire or chain pull (not shown), is set in motion, said transmission element being operatively connected at the distal end to a drive roller 40 mounted rotatably on the bearing block 38.

By way of the transmission element designed as a Bowden wire or chain pull, the rotation movement of the rotary wheel 20 is transmitted to the drive roller 40, which is connected in a rotationally fixed manner to one of the bolts 35 forming the pivot axis 23, such that the rotation of the drive roller 40 causes the tool tip 6 to pivot relative to the longitudinal axis 14 of the shaft 2 and about the pivot axis 23.

The guide rollers 39 mounted in the bearing block 38 serve to laterally guide the pull cable 10. The base 37c forming the proximal end of the sleeve 37 is mounted between the sides 38a of the bearing block 38 such that it can follow the pivoting movement about the pivot axis 23 and slides to and fro between the sides 38a of the bearing block 38.

It is also possible, during the pivoting of the tool tip 6 relative to the longitudinal axis 14 of the shaft 2, for the jaw parts 8 and 9 of the tool 7 to be closed and opened again by actuation of the grip 13 mounted on the handle 4.

A medical instrument 1 as described above is characterized in that the pull cable 10 is reliably protected against torsion during the rotation of the tool tip 6 about the longitudinal axis 14 of the shaft 2.

The invention claimed is:

1. A medical instrument comprising a hollow shaft, at the proximal end of which a handle is arranged, and at the distal end of which a tool tip is arranged, wherein the tool tip has a tool that can be actuated via a spring-loaded pull cable, and wherein the tool tip is rotatable about a longitudinal axis of the shaft and is mounted on the shaft such that the tool tip can be angled with respect to the longitudinal axis of the shaft, wherein the actuation of the pull cable as well as the rotation and angled positioning of the tool tip each take place via separate drives, which are arranged on the handle,
   wherein an anti-twist means protecting the pull cable against torsion is arranged on a distal end of the pull cable arranged in the tool tip rotatable about the longitudinal axis of the shaft, wherein the anti-twist means is mounted at least partially on the shaft,
   wherein the anti-twist means is constructed in two parts and is composed of a first part connected to the pull cable and of a second part mounted on the shaft, wherein both parts of the anti-twist means are operatively connected to each other in such a way that the second part blocks a rotation of the first part relative to the second part.

2. The medical instrument according to claim 1, wherein the first part of the anti-twist means connected to the pull cable is designed as a tube coaxially enclosing the pull cable, and in that the second part of the anti-twist means mounted on the shaft is designed as a sleeve engaging at least partially around the tube.

3. The medical instrument according to claim 2, further comprising:
   an oblong hole which extends in the direction of the longitudinal axis of the shaft and is formed in the tube of the first part of the anti-twist means, and a radially extending pin which protrudes into the oblong hole of the tube and is arranged in the sleeve of the second part of the anti-twist means.

4. The medical instrument according to claim 2, wherein the two parts of the anti-twist means are movable relative to each other in the direction of the longitudinal axis of the shaft.

5. The medical instrument according to claim 2, wherein the tube forming the first part of the anti-twist means has an outer contour that is non-circular in cross section, and in that the sleeve forming the second part of the anti-twist means has, in an area engaging around the tube, an inner surface contour which forms a corresponding matching contour to the outer contour of the tube in this engaged area.

6. The medical instrument according to claim 5, wherein the tube forming the first part of the anti-twist means has, on its outer circumferential surface, two flat portions extending in the direction of the longitudinal axis of the shaft, and in that the sleeve forming the second part of the anti-twist means has, in the area engaging around the tube, two corresponding flat portions on the inner face directed toward the tube.

7. The medical instrument according to claim 6, wherein the flat portions formed on the outer circumferential surface of the tube are offset to each other by 180°.

8. A medical instrument comprising a hollow shaft, at the proximal end of which a handle is arranged, and at the distal end of which a tool tip is arranged, wherein the tool tip has a tool that can be actuated via a spring-loaded pull cable, and wherein the tool tip is rotatable about a longitudinal axis of the shaft and is mounted on the shaft such that the tool tip can be angled with respect to the longitudinal axis of the shaft, wherein the actuation of the pull cable as well as the rotation and angled position of the tool tip each take place via separate drives, which are arranged oh the handle,
   wherein an anti-twist means protecting the pull cable against torsion is arranged on the distal end of the pull cable arranged in the tool tip rotatable about the longitudinal axis of the shaft, wherein the anti-twist means is mounted at least partially on the shaft,
   wherein the anti-twist means is constructed in two parts and is composed of a first part connected to the pull cable and of a second part mounted on the shaft, wherein both parts of the anti-twist means are operatively connected to each other in such a way that the second part blocks a rotation of the first part relative to the second part, and
   wherein the two parts of the anti-twist means are movable relative to each other in the direction of the longitudinal axis of the shaft.

9. The medical instrument according to claim 8, wherein the tube forming the first part of the anti-twist means has an outer contour that is non-circular in cross section, and in that the sleeve forming the second part of the anti-twist means has, in the area engaging around the tube, an inner surface contour which forms a corresponding matching contour to the outer contour of the tube in this engaged area.

10. The medical instrument according claim 8, further comprising:
   an oblong hole which extends in the direction of the longitudinal axis of the shaft and is formed in the tube of the first part of the anti-twist means, and
   a radially extending pin which protrudes into the oblong hole of the tube and is arranged in the sleeve of the second part of the anti-twist means.

* * * * *